United States Patent
Palla-Venkata et al.

(10) Patent No.: US 8,778,910 B2
(45) Date of Patent: Jul. 15, 2014

(54) CONCENTRATED LAMELLAR LIQUID PERSONAL CLEANSING COMPOSITION

(71) Applicant: Conopco, Inc., Englewood Cliffs, NJ (US)

(72) Inventors: Chandra Sekhar Palla-Venkata, Trumbull, CT (US); Yuntao Thomas Hu, Orange, CT (US); Kevin David Hermanson, Trumbull, CT (US); Rajendra Mohanlal Dave, Trumbull, CT (US); Lin Yang, Trumbull, CT (US); James Andrew Early, Trumbull, CT (US); Alexander Kingston Shutak, Trumbull, CT (US); Anat Shiloach, Trumbull, CT (US); Teanoosh Moaddel, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/708,012

(22) Filed: Dec. 7, 2012

(65) Prior Publication Data
US 2014/0162979 A1 Jun. 12, 2014

(51) Int. Cl.
*A61K 6/00* (2006.01)

(52) U.S. Cl.
USPC .......................................................... 514/63

(58) Field of Classification Search
None
See application file for complete search history.

(56) References Cited

U.S. PATENT DOCUMENTS

| | | | |
|---|---|---|---|
| 5,308,526 A * | 5/1994 | Dias et al. ...................... | 510/159 |
| 5,952,286 A * | 9/1999 | Puvvada et al. ................ | 510/417 |
| 7,879,781 B2 * | 2/2011 | Patel et al. ..................... | 510/130 |
| 7,884,060 B1 | 2/2011 | Hermanson et al. | |
| 7,884,061 B1 | 2/2011 | Hermanson et al. | |
| 8,110,533 B1 | 2/2012 | Tsaur | |
| 8,114,826 B1 | 2/2012 | Hermanson et al. | |
| 2007/0287648 A1 | 12/2007 | Moaddel et al. | |
| 2008/0193405 A1 * | 8/2008 | Mukherjee et al. ......... | 424/70.16 |
| 2010/0183692 A1 * | 7/2010 | Natsch ........................... | 424/405 |

FOREIGN PATENT DOCUMENTS

WO WO 2010/012582 A3 * 2/2010 ............... A61K 8/31

OTHER PUBLICATIONS

Colafemmina et al, Lauri Acid-Induced Formation of a Lyotropic Nematic Phase of Disk-Shaped Micelles, J. Phys. Chem. B, 2010, pp. 7250-7260, vol. 114.

* cited by examiner

*Primary Examiner* — San-Ming Hui
*Assistant Examiner* — Jeanmarie Calvillo
(74) *Attorney, Agent, or Firm* — Alan A. Bornstein

(57) ABSTRACT

The invention relates to concentrated liquid cleansing compositions in lamellar phase which possess a lotion-like appearance conveying signals of enhanced moisturization. The use of a specific ratio of synthetic anionic surfactant(s) and co-surfactant(s) to fatty acid(s) in a structured liquid product was found to improve lather production by moderating or eliminating the increase in viscosity upon dilution. In a further embodiment, specific small hydrophobic molecules were found to improve freeze/thaw stability and thereby cause the inventive composition to maintain noticeable moisturization signals.

14 Claims, No Drawings

CONCENTRATED LAMELLAR LIQUID PERSONAL CLEANSING COMPOSITION

BACKGROUND OF THE INVENTION

1. Field of the Invention

The present invention relates to concentrated liquid cleansing compositions suitable for topical application for cleansing the human body, such as the skin and hair. In particular, it relates to a concentrated, lamellar phase personal cleansing composition that is able to lather appreciably and in a preferred embodiment resist freeze-thaw destabilization.

2. Background of the Art

Concentrated lamellar phase liquid cleansers are known, For example U.S. Pat. Nos. 7,884,060 and 7,884,061 issued on Feb. 14, 2012 and 8,114,826, issued on Feb. 8, 2011 all to Hermanson et. al. disclose preparing concentrated, readily pumpable soap based formulations containing greater than 40% of fatty acid(s).

U.S. Pat. No. 7,879,781 issued on February, 2011 to Patel et al. discloses preparing high emollient lamellar compositions consisting of 2-4% lauric acid resistant to viscosity changes under freeze-thaw cycles.

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod-micellar solutions are more viscous because movement of the longer micelles is restricted. At a critical shear rate, the micelles align and the solution becomes shear thinning. Addition of salts increases the size of the rod-micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 titled "Liquid Cleansing Composition Comprising Soluble, Lamellar Phase Inducing Structurant" by Sudhakar Puvvada, et al., issued Sep. 14, 1999. Generally, the transition from micellar to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

One problem with certain lamellar phase compositions is that they tend to lose their lamellar stability in colder temperatures (e.g., 0 to 45 degree F.). While not wishing to be bound by theory, this may be because, in cold conditions, the oil droplets become less flexible and the spherical structure characterizing the lamellar interaction breaks into lamellar sheets instead.

Specific inventive concentrated lamellar cleansing compositions were unexpectedly discovered that provide consumers with (a) better in-use sensory properties such as creamy appearing lather and improved skin feel such as providing a moisturized feeling to the skin (b) better performance such as increasing the amount of lather and the speed to lather and (c) potentially offering more number of washes with a smaller pack/product for the user. The invention provides a concentrated cleansing composition characterized by a soft lamellar gel with a buffer-like feel and good spreadability with high levels of fatty acid(s) in a specific ratio range to synthetic anionic surfactants and cosurfactants. In a preferred embodiment, the inventive composition was unexpectedly found to be stabilized against a pronounced loss of viscosity after freezing and thawing by a selection of small hydrophobic molecules.

Concentrated cleansing compositions are known to go through undesired, very viscous phases (cubic and hexagonal phases) before the more desired, easy to handle, less viscous lamellar phase is reached upon increase of surfactant concentration (see e.g. U.S. 2007/0287648 to Moaddel et al, incorporated herein by reference). Co surfactants (herein defined as amphoteric or non-ionic surfactants or blends thereof) may be used to facilitate the formation of the lamellar phases. In the inventive concentrated formulations, a specific ratio range of synthetic anionic surfactant(s) and co-surfactant(s) to $C_{12}$ to $C_{18}$ fatty acid(s) was seen to allow the formation of lamellar phase and unexpectedly provide substantially improved lather volume and speed to lather. At these high levels of fatty acid content, though a soft lamellar gel is formed that is stable at room and high temperatures, an unusually large drop in viscosity (>95%) under freeze-thaw conditions was noted. In a preferred embodiment, it was unexpectedly found that the addition of specific, small, hydrophobic molecules substantially improved the freeze-thaw stability of the concentrated high fatty acid containing compositions that is essential in beneficial consumer use of the product.

BRIEF DESCRIPTION OF THE INVENTION

In one aspect of the invention is an aqueous, lamellar structured, skin cleaning composition including but not limited to:
a. about 15 to 40% by wt. of synthetic anionic surfactant(s);
b. about 5 to 30% by wt. of co-surfactant(s) selected from the group of amphoteric or nonionic surfactants or blends thereof;
c. about 5 to 15% by wt. of $C_{12}$ to $C_{18}$ linear alkyl fatty acid(s);
d. wherein the synthetic anionic surfactant(s): co-surfactant(s) ratio is about 0.5 to 3; and
e. wherein the synthetic anionic surfactant(s) and co-surfactant(s) to $C_{12}$ to $C_{16}$ linear alkyl fatty acid(s) ratio is about 2 to 6.

DETAILED DESCRIPTION OF THE INVENTION

In one aspect of the invention is an aqueous, lamellar structured, skin cleaning composition including but not limited to:
a. about 15 to 40% by wt. of synthetic anionic surfactant(s); preferably a minimum of about 17.5 or 20% by wt. and a maximum of about 30 or 35% by wt.;
b. about 5 to 30% by wt, of co-surfactant(s) selected from the group of amphoteric or nonionic surfactants or blends thereof; preferably a minimum of about 7.5 or 10% by wt, and a maximum of about 20 or 25% by wt.; preferably the co surfactant is sodium lauroyl amphoacetate, cocamidopropyl betaine, cocamidopropyl hydroxyl sultaine or alkylpoly glucoside or blends thereof;
c. about 5 to 15% by wt. of $C_{12}$ to $C_{18}$ linear alkyl fatty acid(s); preferably lauric, myristic, palmitic or stearic acid or blends thereof; more preferably lauric acid; more preferably greater than about 7 or 8% by wt, and less than about 11 or 12% by wt.
d. wherein the synthetic anionic surfactant(s) : co-surfactant(s) ratio is about 0.5 to 3; preferably a minimum of about 0.5, 0.55 or 0.6 and a maximum of about 2, 2.5 or 3; and
e. wherein the synthetic anionic surfactant(s) and co-surfactant(s) to $C_{12}$ to $C_{18}$ linear alkyl fatty acid(s) ratio is about 2 to 6; preferably about 2 to 4; and more preferably about 2 to 3.5.

Advantageously the viscosity either decreases continuously or only slightly increases by no more than 3, 2 or 1 Pa.s as the inventive composition is diluted with water during skin cleansing and rinsing by a consumer at 40 C. (warm water) compared to comparative compositions which show a significant viscosity increase during dilution via rinsing and deleterious lather production/stability. Preferably the pH of the inventive composition is in the range of about 5 to 8, more preferably 5.5 to 7.7 and most preferably 6 to 7.5.

Preferably the inventive composition further includes an effective amount of freeze-thaw stabilizer(s) selected from branched $C_6$ to $C_{18}$ alkenes, branched $C_6$ to $C_{18}$ alkenols, branched $C_6$ to $C_{18}$ alkanols, branched $C_6$ to $C_{18}$ alkanes, branched $C_6$ to $C_{18}$ alkyl aryl ethers, benzyl esters and blends thereof in a concentration effective for maintaining at least 55% of the viscosity of the composition after one freeze-thaw cycle using the standard freeze-thaw test More preferably the freeze-thaw stabilizer(s) are present in a total concentration of about 0.5 to 5% by wt.; preferably a minimum of about 1 or 1.5% by wt. and a maximum of about 3 or 4% by wt.

Most preferably the freeze thaw stabilizer(s) are selected from dihydromyrcenol, isooctanol, linalool, citronellol, 1-octene-3-ol, hexyl acetate, limonene, octylphenoxy polyethoxy ethanol (Igepal®), lillial, hexane, 1-octene, and benzyl salicylate and blends thereof.

Advantageously the inventive freeze-thaw stabilizer(s) have an HLB value of less than about 5. Preferably the freeze-thaw stabilizer(s) have an effective molecular length of greater than about 5 but no greater than about 30 Angstroms. More preferably the freeze-thaw stabilizer(s) have a melting point less than 0 C. Most preferably the inventive freeze-thaw stabilizer(s) have at least two of these properties and in a preferred embodiment have all three of these properties.

In another preferred embodiment, the inventive composition includes about 0.5 to 3% by wt. of 12-Hydroxy stearic acid.

Preferably the inventive composition includes non-occlusive emollients in the concentration range of about 0.5 to 25% by wt; preferably a minimum of about 2.5 or 5% by wt. and a maximum of about 15 or 20% by wt. More preferably the non-occlusive emollients are selected from glycerin or 1, 3 butanediol or blends thereof.

Preferably the inventive composition includes occlusive emollients in the concentration range of about 0.5 to 25% by wt.; preferably a minimum of about 2.5 or 5% by wt, and a maximum of about 15 or 20% by wt. More preferably the occlusive emollients are selected from mineral oils, tri and diglyceride oils, silicone oils, Petrolatum, or paraffin wax or blends thereof.

Advantageously the synthetic anionic surfactant(s) are selected from sodium lauryl ether sulfate-1EO, 2EO and 3EO, $C_{12}$ acyl glycinate, Directly Esterified Fatty Isethionate (DEFI) or sodium trideceth sulfate or blends thereof and the co-surfactant(s) are selected from cocamidopropyl betaine (CAPB), Amphoacetate, cocamidopropyl hydroxyl sultaine (CAPHS) alkylpoly glucoside (APG) or blends thereof.

Surfactants:

Synthetic anionic surfactant(s) and co-surfactant(s) are preferably included in the inventive cleansing composition. Surfactants are compounds that have hydrophobic and hydrophilic portions that act to reduce the surface tension of the aqueous solutions they are dissolved in.

Synthetic Anionic Surfactant(s):

The cleansing composition of the present invention preferably contains one or more non-soap, synthetic anionic surfactant(s). Synthetic anionic surfactant(s) are preferably used at levels as low as 15, 17.5 or 20% by wt. and at levels as high as 30, 35 or 40% by wt.

The synthetic anionic detergent active which may be used in the invention may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-C22 hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl haying 8 to 18 carbons, preferably 12 to 18 carbons, n has an average value of greater than 1.0, preferably lesser than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_8$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M;\ and$$

amide-MEA sulfosuccinates of the formula;

$$R^4CONHCH_2CH_2O_2CCH_2CH(SO_3M)CO_2M$$

wherein $R^4$ ranges from $C_8$-$C_2$ alkyl and M is a solubilizing cation.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic carboxylic acids having from 6 to 18 carbon atoms and an iodine value of less than 20. At least 75% of the mixed carboxylic acids have from 12 to 18 carbon atoms and up to 25% have from 6 to 10 carbon atoms.

The acyl isethionate may be an alkoxylated isethionate such as is described in Ilardi et at, U.S. Pat. No. 5,393,466, titled "Fatty Acid Esters of Polyalkoxylated isethonic acid; issued Feb. 28, 1995; hereby incorporated by reference. This compound has the general formula:

$$R\ C\text{-}O\ (O)\text{-}C(X)H\text{-}C(Y)H_2\text{-}(OCH\text{-}CH_2)_m\text{-}SO_3M^{30}$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric Surfactants

One or more amphoteric surfactant(s) may be used in this invention as a co-surfactant. Amphoteric surfactant(s) are preferably used at levels as low as 57.5 or 10% by wt. and at levels as high as 20, 25or 30% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1\text{-}[\text{-}C(O)\text{-}NH\ (CH_2)_n\text{-}]_m\text{-}N^+\text{-}(R^2)(R^3)X\text{-}Y$$

wherein $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is -$CO_2$- or -$SO_3$-

Suitable amphoteric surfactants within the above general formula include simple betaines of formula:

$$R^1\text{-}N^+\text{-}(R^2)(R^3)CH_2CO_2^-$$

and amido betaines of formula:

$$R^1\text{-}CONH(CH_2)_n\text{-}N^+\text{-}(R^2)(R^3)CH_2CO_2^-$$

wherein n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups R' have 10 to 14 carbon atoms. $R^2$ and $R^3$ are preferably methyl.

A further possibility is that the amphoteric detergent is a sulphobetaine of formula:

$$R^1\text{-}N^+\text{-}(R^2)(R^3)(CH_2)_3SO_3^-$$

Or $$R^1\text{-}CONH(CH_2)_m\text{-}N^+\text{-}(R^2)(R^3)(CH_2)_3SO_3^-$$

wherein m is 2 or 3, or variants of these in which -$(CH_2)_3$ $SO_3^-$ is replaced by $$\text{-CH2C(OH)(H)CH}_2SO_3^-$$

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactant(s) may be used in the cleansing composition of the present invention as a co-surfactant, Nonionic surfactants are preferably used at levels as low as 5, 7.5 or 10% by wt. and at levels as high as 20, 25 or 30% by wt. The nonionic surfactants which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include alkylpolyglucosides and carboxylic acid/alcohol ethoxylates having the following structures a) $HOCH_2(CH_2)n(CH_2CH_2O)_x H$ or b) $HOOC(CH_2)_m(CH_2CH_2O)_y H$;

where m, n are independently <18; and x, y are independently >1; preferably m, n are independently 6 to 18; x, y are independently 1 to 30;

c) $HOOC(CH_2)_i\text{-}CH{=}CH\text{-}(CH_2)_k(CH_2CH_2O)_z H$;

where i, k are independently 5 to 15; and z is independently 5 to 50; preferably i, k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant System" issued Apr. 23, 1991; hereby incorporated into the subject application by reference.

Normal Carboxylic Acids

Normal $C_{12}$-$C_{18}$ alkyl carboxylic acid(s) are preferably used for the invention, Preferably carboxylic acid(s), such as lauric ($C_{12}$), myristic ($C_{14}$) or palmitic ($C_{16}$) acids are used alone or in combination. Advantageously the carboxylic acid(s) are used at levels as low as 7 or 8% by wt. and at levels as high as 11 or 12% by wt.

Freeze-thaw Stabilizer Compounds

In a preferred embodiment, one or a blend of small hydrophobic compounds are preferably used in the invention to stabilize the composition against substantial loss in viscosity during freeze-thaw cycle. Useful compounds include branched $C_6$ to $C_{18}$ alkenes, branched $C_6$ to $C_{18}$ alkenols, branched $C_6$ to $C_{18}$ alkanols, branched $C_6$ to $C_{18}$ alkanes, branched $C_6$ to $C_{16}$ alkyl aryl ethers, benzyl esters and blends thereof for maintaining at least 55% of the viscosity of the composition after one freeze-thaw cycle using the standard freeze-thaw test described below.

Useful compounds include the following:

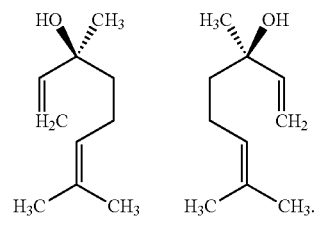

linalool

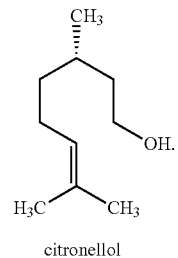

citronellol

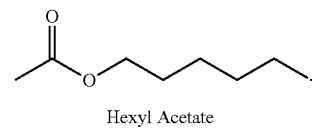

Hexyl Acetate

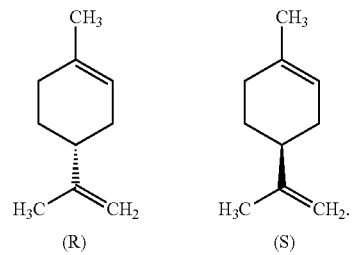

Limonene

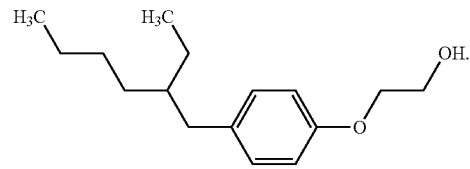

Polyoxyethylene(2) isooctylphenyl ether

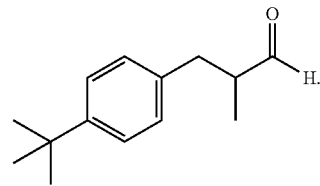

Lillial;
2-(4-tert-Butylbenzyl)propionaldehyde

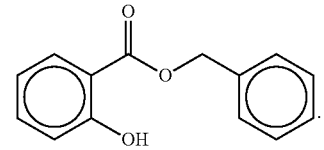

Benzyl salicylate

Other suitable compounds include Isooctanol, isotridecanol, and/or isodecanol and the like.

Cationic Skin Conditioning Agents

A useful component in compositions according to the invention is a cationic skin feel agent or polymer, such as for example cationic celluloses. Cationic polymers are preferably used at levels as low as about 0.1 to 2% up to levels as high as the solubility limit of the specific polymer, or preferably up to about 4 to 5% by wt., provided that the solubility limit of the particular cationic polymer or blend thereof is not exceeded.

Cationic cellulose is available from Amerchol Corp. (Edison, N.J., U.S.A.) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., U.S.A.) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their Jaguar (r) trademark series). Examples are Jaguar (r) C-13S, which has a low degree of substitution of the cationic groups and high viscosity, Jaguar (r) C15, having a moderate degree of substitution and a low viscosity, Jaguar (r) C17 (high degree of substitution, high viscosity), Jaguar (r) C16, which is a hydroxypropylated cationic guar derivative containing a low level of substituent groups as well as cationic quaternary ammonium groups, and Jaguar (r) 162 which is a high transparency, medium viscosity guar having a low degree of substitution.

Particularly preferred cationic polymers are Jaguar (r) C13S, Jaguar (r) C15, Jaguar (r) C17 and Jaguar (r) C16 and Jaguar (r) C-162, especially Jaguar (r) C13S, and Jaguar (r) C-14/BFG. The Jaguar (r) C14/BFG material is the same molecule as Jaguar (r) C13, except that a glyoxal cross linker has replaced the boron. Other cationic skin feel agents known in the art may be used provided that they are compatible with the inventive formulation.

Other suitable examples of surfactants described above which may be used are described in "Surface Active Agents and Detergents" (Vol. I & II) by Schwartz, Perry & Berch, incorporated into the subject application by reference in its entirety.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and soluble coloring agents, and the like; all of which are useful in enhancing the appearance or cosmetic properties of the product.

The compositions may further comprise antimicrobials such as 2-hydroxy-4,2', 4' trichlorodiphenylether (DP300); preservatives such as methylisothiazolinone/methylchloroisothiazolinone (Kathon, MIT), dimethyloldimethylhydantoin/iodopropynyl butylcarbamate (Glydant XL1000,), parabens, sorbic acid etc, and the like.

The compositions may also comprise coconut acyl mono or diethanol amides as suds boosters, and strongly ionizing salts such as sodium chloride and sodium sulfate may also be used to advantage for increasing viscosity. Preferably strongly ionizing salts, otherwise known as electrolytes, will be present at less than 5, 4, 3, or 1% by wt.

Antioxidants such as, for example, butylated hydroxytoluene (BHT) and the like may be used advantageously in amounts of about 0.01% or higher if appropriate.

Emollients

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Moisturizers that also are Humectants such as polyhydric alcohols, e.g. glycerin and propylene glycol, and the like; and polyols such as the polyethylene glycols such as Polyox WSR N-60K (PEG-45M) and the like are used in a preferred embodiment of the invention. Humectants are preferably used at a minimum of 0.5, 2.5 or 5% by wt. and a maximum of 15, 20 or 25% by wt.

Hydrophobic emollients are used in a preferred embodiment of the invention. Preferred are hydrophobic emollient(s) with weight average particle sizes below either 1000 or 500 microns in diameter and are defined herein as "finely dispersed oils". These emollients are preferably used at a minimum of 0.5, 2.5 or 5% by wt. and a maximum of 15, 20 or 25% by wt.

Suitable hydrophobic emollients include but are not limited to the following:

(a) silicone oils and modifications thereof such as linear and cyclic polydimethylsiloxanes; amino, alkyl, alkylaryl, and aryl silicone oils;

(b) fats and oils including natural fats and oils (triglycerides) such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plat extracts;

(e) hydrocarbons such as petrolatum, polybutene, liquid paraffins, microcrystalline wax ceresin, squalene, pristan and mineral oil;

(f) higher alcohols such as lauryl, cetyl, stearyl, oleyl, behenyl, cholesterol and 2-hexydecanol alcohol;

(g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(h) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(i) mixtures of any of he foregoing components, and the like.

Optional active agents

Advantageously, active agents other than conditioning agents such as emollients or moisturizers defined above may be added to the cleansing composition in a safe and effective amount during formulation to treat the skin during the use of the product. Suitable active ingredients include those that are water soluble or are dispersible within the limits provided above. Suitable active agents may be advantageously selected from antimicrobial and antifungal actives, vitamins, anti-acne actives; anti-wrinkle, anti-skin atrophy and skin repair actives; skin barrier repair actives; non- steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0,01% to about 25% more preferably from about 0.05% to about 15%, even more preferably 0.1% to about 10%, and most preferably 0.1%% to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retina retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p- methoxycinnamate, 2-ethylhexyl N,N-dimethyl-p-aminobenzoate, p- aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilazine and trimeprazine, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Solid particulate optical modifiers

A useful optional component of compositions according to the present invention is one or more solid particulate optical modifiers, preferably light reflecting platelet shaped or platy particles. These particles will preferably have an average particle size $D_{50}$ ranging from about 25,000 to about 150,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles may be at least about 1.8, generally from about 1.9 to about 4, e.g. from about 2 to about 3, and between about 2.5 and 2.8.

Illustrative but not limiting examples of light reflecting particles are bismuth oxychloride (single crystal platelets) and titanium dioxide and/or iron oxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$-$C_{40}$ alkyl ester such as in Biron® Liquid Silver.

Among the suitable titanium dioxide coated mica platelets are materials available from EM Industries, Inc. These include Timiron® MP-45 (particle size range 49,000-57,000 nm), Timiron® MP-99 (particle size range 47,000-57,000 nm), Timiron® MP-47 (particle size range 28,000-38,000 nm), Timiron® MP-149 (particle size range 65,000-82,000 nm), and Timiron® MP-18 (particle size range 41,000-51,000 nm). The weight ratio of titanium dioxide coating to the mica platelet may range from about 1:10 to about 5:1, preferably from about 1:6 to about 1:7, by weight. Advantageously the compositions will generally be substantially free of titanium dioxide outside of that required for coating mica.

Among the suitable iron oxide and titanium dioxide coated mica platelets are materials available from EM Industries, Inc. These include Timiron® MP-28 (particle size range 27,000-37,000 nm), Timiron® MP-29 (particle size range 47,000-55,000 nm), and Timiron® MP-24 (particle size range 56,000-70,000 nm).

Among the suitable iron oxide coated mica platelets are materials available from EM Industries, Inc. These include Colorona® Bronze Sparkle (particle size range 28,000-42,000 nm), Colorona® Glitter Bronze (particle size range 65,000-82,000 nm), Colorona® Copper Sparkle (particle size range 25,000-39,000 nm), and Colorona® Glitter Copper (particle size range 65,000-82,000 nm).

Suitable coatings for mica other than titanium dioxide and iron oxide may also achieve the appropriate optical properties required for the present invention. These types of coated micas must also meet the refractive index of at least about 1.8. Other coatings include silica on the mica platelets.

Exfoliants

The inventive composition may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads; and the like. These exfoliants come in a variety of particle sizes and morphology ranging from micron sized to a few mm. They also have a range of hardness. Some examples are given in table 1 below.

TABLE A

| Material | Hardness (Mohs) |
|---|---|
| Talc | 1 |
| Calcite | 3 |
| Pumice | 4-6 |
| Walnut Shells | 3-4 |
| Dolomite | 4 |
| Polyethylene | ~1 |

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Example 1:

Several inventive and comparative compositions were prepared according to Table 1 and the dilution profile and lather profile was measured for each according to the methods provided below. The data is listed in Table 2.

Inventive compositions showed that with addition of lauric acid in a synthetic anionic surfactant(s)+co-surfactant(s): fatty acid(s) ratio of about 2 to 6, the viscosity build up on dilution either decreased or only slightly increased thus improving speed to lather and lather volume.

TABLE 1

| Ingredients | Sample 1 Comparative | Sample 2 Comparative | Sample 3 Inventive | Sample 4 Inventive |
|---|---|---|---|---|
| Sodium lauryl ether sulfate (1) | 20 | 20 | 20 | 20 |
| Sodium Lauroyl Amphoacetate (2) | 10 | 10 | 10 | 10 |
| Lauric Acid (3) | 0 | 3 | 5 | 9 |
| Water | Up to 100 | Up to 100 | Up to 100 | Up to 100 |
| Synthetic anionic surfactant(s): co-surfactant(s) ratio | 2 | 2 | 2 | 2 |
| Synthetic anionic surfactant(s) and co-surfactant(s) to C12 to C18 linear alkyl fatty acid(s) ratio | Not defined | 10 | 6 | 3.33 |

(1) Sodium lauryl ether sulfate (Trade name. Texapon N701) obtained from BASF (Florham Park, NJ 07932, USA)
(2) Sodium lauroyl amphoacetate (Trade Name: Miranol Ultra L-32) obtained from Rhodia (8 Cedar Brook Dove, Cranbury, NJ 08512-7500, USA)
(3) Lauric Acid (Trade name Edenor C12-98-100) obtained from Emery Oleochemicals (4900 Este Avenue, 45232 Cincinnati, Ohio, USA)

TABLE 2

| Surfactant Concentration including LA | Viscosity (Pa.s) at 1 1/s | | | |
|---|---|---|---|---|
| (wt %) (details in Table 1) | Sample 1 Comparative | Sample 2 Comparative | Sample 3 Inventive | Sample 4 Inventive |
| 39 | | | | 130 |
| 35 | | | 32.1 | |
| 33 | | 12.6 | | |
| 30 | 1.73 | | | |
| 20 | 1.64 | 0.556 | 0.268 | 0.817 |
| 15 | 104 | 3.61 | 0.538 | 0.0596 |
| 7 | 0.272 | 0.088 | 0.0133 | 0.031 |
| Speed to Lather (on a scale of 5) | 2 | 2 | 4 | 5 |
| Amount of Lather (on a scale of 5) | 2 | 3 | 4 | 5 |

Example 2:

A series of samples were prepared as provided in Table 3 with inventive freeze thaw stabilizers shown in Table 4 and compared to comparative materials as shown in Table 5. The inventive freeze thaw stabilizers were seen to provide protection from a drop in viscosity of no more than 55% using the freeze-thaw method described below.

Method of preparation: All the formulas in Tables 1-3, 6 and 8 were prepared by the using the following procedure:

1. Add water and fatty acid(s) (including hydroxyl stearic acid if present) and heated up to 80 C.
2. Add polyols such as PPG-9
3. Mix until all the fatty acid(s) are melted
4. Add primary synthetic anionic surfactant/s and mix until uniform
5. Add secondary co-surfactant(s) and mix until uniform
6. Add the optional emollients and occlusive agents
7. Start decreasing the temperature
8. Add freeze-thaw additives at 60 C.
9, Add preservatives and fragrance below 40 C.
10. Cool and mix until homogeneously uniform

TABLE 3

Formulation Details: Sample Formula A

| Ingredients | Wt % |
|---|---|
| Sodium lauryl ether sulfate | 20 |
| Sodium Lauroyl Amphoacetate (AA) | 10 |
| Lauric Acid | 9 |
| PPG-9 | 2 |
| Freeze-thaw Additives | 0~5 |
| Synthetic anionic surfactant(s): co-surfactant(s) ratio | 2 |
| Synthetic anionic surfactant(s) and co-surfactant(s) to $C_{12}$ to $C_{18}$ linear alkyl fatty acid(s) ratio | 3.33 |

TABLE 4

Shows examples containing a selection of inventive compounds that have provided freeze-thaw stability when present at 2-3% levels in a typical concentrated lamellar composition given in Table 3

| Freeze-thaw (F/T) additive | Wt % (F/T) additive in Sample A | RT Viscosity (10 Hz) - Pa.s | Viscosity @ RT* after 1 F/T cycle (10 Hz) - Pa.s | % drop in viscosity |
|---|---|---|---|---|
| Dihydromyrcenol | 2 | 13.5 | 11.6 | 14 |
| Isodecanol | 2 | 12.4 | 10.4 | 16 |
| Isooctanol | 2 | 14.2 | 11.6 | 18 |
| Isotridecanol | 2 | 13.4 | 10.8 | 21 |
| Linalool | 2 | 13.5 | 10.5 | 22 |
| Citronellol | 2 | 20.1 | 14.9 | 26 |
| 1-Octene-3-ol | 2 | 17.3 | 12.6 | 27 |
| Hexyl Acetate | 2 | 19.3 | 12.9 | 33 |
| Limonene | 2 | 16.5 | 10.9 | 34 |
| Polyoxyethylene(2) isooctylphenyl ether (Igepal CA-210) | 2 | 12.5 | 8.05 | 36 |
| Lillial | 2 | 17.4 | 11.1 | 36 |
| Hexane | 2 | 14.1 | 8.77 | 38 |
| 1-Octene | 2 | 13.4 | 8.22 | 39 |
| Benzyl Salicylate | 2 | 19.9 | 9.1 | 54 |

*RT = room temperature or about 22° C.

TABLE 5

Shows examples containing a selection of comparative compounds that did not provide substantial freeze-thaw stability (compared to a control "no additive") when present at 2-3% levels in a typical concentrated lamellar composition given in Table 3

| Freeze-thaw (F/T) additive | Wt % (F/T) additive in Sample A | RT Viscosity (10 Hz) - Pa.s | Viscosity @ RT after 1 F/T cycle (10Hz) - Pa.s | % drop in viscosity |
| --- | --- | --- | --- | --- |
| Octane | 2 | 14.1 | 3.34 | 76 |
| Octanol | 2 | 20.7 | 4.58 | 78 |
| lauryl alcohol | 2 | 38.6 | 2.95 | 92 |
| Sodium 2-Ethylhexyl Sulfate | 2 | 8.6 | 0.631 | 93 |
| Dipropylene glycol (DPG) | 2 | 12.2 | 0.53 | 96 |
| Sodium Xylene Sulfonate | 0.5 | 16.1 | 0.616 | 96 |
| No Additive | 0 | 11.8 | 0.302 | 97 |
| Decane | 2 | 25.1 | 0.546 | 98 |
| Sorbitol | 3 | 17.6 | 0.378 | 98 |
| Isostearyl alcohol | 2 | 37.2 | 0.769 | 98 |
| Oleic acid | 2 | 27.7 | 0.388 | 99 |
| Capric Caprilic Triglyceride (CCT) | 2 | 66 | 0.907 | 99 |

Example 3:

A series of inventive and comparative samples in a further preferred embodiment of the invention provided in Table 6 were prepared with hydroxy stearic acid and inventive freeze thaw stabilizer materials and compared to the same samples with comparative material(s) as described in Table 7. All the inventive freeze thaw stabilizer materials were seen to provide protection from a drop in viscosity of no more than 55% even in the formulations containing hydroxy stearic acid (Sample formula B) using the freeze-thaw method described below

TABLE 6

| Formulation details: Sample Formula B | |
| --- | --- |
| Ingredients | Wt % |
| sodium lauryl ether sulfate | 20 |
| Sodium lauroyl Amphoacetate (AA) | 10 |
| Lauric Acid | 9 |
| 12-Hydroxystearic acid | 2 |
| PPG-9 | 2 |
| Freeze-thaw Additives | 0-5 |
| Synthetic anionic surfactant(s): co-surfactant(s) ratio | 2 |
| Synthetic anionic surfactant(s) and co-surfactant(s) to $C_{12}$ to $C_{18}$ linear alkyl fatty acid(s) ratio | 3.33 |

TABLE 7

Shows a sampling of well known freeze-thaw additives comparing inventive examples and comparative examples (and a control) in a concentrated lamellar composition with hydroxyl stearic acid as in sample formula B

| Freeze-thaw (F/T) additive | Wt % (F/T) additive in Sample B | RT Viscosity (10 Hz) - Pa.s | Viscosity @ RT after 1 F/T cycle (10 Hz) - Pa.s | % drop in viscosity |
| --- | --- | --- | --- | --- |
| Dihydromyrcenol | 2 | 13.5 | 11.6 | 14 |
| DPG | 2 | 75.4 | 0.753 | 99 |
| Lauryl Alcohol | 2 | 38.6 | 2.95 | 92 |
| NaCl | 1.5 | 25.4 | 0.907 | 96 |
| No additive (Control) | 0 | 12.2 | 0.881 | 93 |

Example 4:

A series of samples of a further preferred embodiment of the invention were prepared as provided in Table 8 with inventive freeze thaw stabilizers shown in Table 9 and compared to comparative materials as shown in Table 10. The inventive freeze thaw stabilizers were seen to provide protection from a drop in viscosity of no more than 55% using the freeze-thaw method described below.

TABLE 8

Shows a further preferred embodiment of the invention containing 25% by wt. of Petrolatum:

| Ingredients | Wt % |
| --- | --- |
| sodium lauryl ether sulfate | 15 |
| Sodium lauroyl Amphoacetate (AA) | 7.5 |
| Lauric Acid | 6.75 |
| Petrolatum | 25 |
| PPG-9 | 1.5 |
| Dihydromyrcenol | 2 |
| Synthetic anionic surfactant(s): co-surfactant(s) ratio | 2 |
| Synthetic anionic surfactant(s) and co surfactant(s) to $C_{12}$ to $C_{18}$ linear alkyl fatty acid(s) ratio | 3.33 |

TABLE 9

Shows selected properties of some of the inventive freeze-thaw materials that provided substantial freeze-thaw stability in the concentrated lamellar compositions of the invention.

| Freeze-thaw additive | Mol. Wt | HLB Value | Length (in Angstroms) | Melting point (C.) |
| --- | --- | --- | --- | --- |
| Dihydromyrcenol | 156 | 0.69 | 11.93 | −24.41 |
| Isooctanol | 130 | 1.89 | 11.53 | −76 |
| Isotridecanol | 200 | 1.89 | 19.04 | <−30 |
| 1-Octene-3-ol | 128 | 2.36 | 12.85 | −49.17 |
| Igepal CA-210 | 294 | 2.7 | 13.6 | |
| Hexane | 86 | <1 | 10.4 | −96 |
| 1-Octene | 112 | <1 | 12.77 | −107 |

TABLE 10

Shows selected properties of some of the comparative materials that did not provide the amount of freeze-thaw stability in the concentrated lamellar compositions of the invention.

| Freeze-thaw additive | Mol. Wt | HLB Value | Length (in Angstroms) | Melting point (C.) |
|---|---|---|---|---|
| lauryl alcohol | 186 | 2.13 | 19.04 | 24 |
| Sodium 2-Ethylhexyl Sulfate | 232 | 24.82 | 14.13 | >15 |
| SXS (sodium xylene sulphonate) | 208 | 25.26 | 10.96 | 27 |
| Sorbitol | 182 | >20 | 10.94 | 95 |
| Isostearyl alcohol | 270 | 1.04 | 25.32 | 0 |
| Oleic acid | 282 | 1.61 | 25.91 | 13 |

Methods:

A) Lather Method

The lather was generated by hand using water at 37 C. The following protocol was used:

a. 1.5 gms of product was dosed on wet hand;

b. 2 gms of additional water was used to dilute and both hands were rubbed to-and-fro 5 times for the lather generation;

c. Speed of lather was qualitatively assessed based on number of rubs needed for lather generation (typically assessed visually after 5 rubs);

d. Additional water was added to further generate lather and after 10-15 rubs, the lather was collected and visually assessed for the amount of lather on a scale of 1-5 where 1 represents no visible lather and 5 represents copious lather.

B) Rheology Method

The following method was used to determine the viscosity.

The viscosities of the samples during dilution process were measured at a shear rate of 1 1/s using a standard rate sweep experiments from 0.1-100 1/s. 50 mm serrated cone with 2° cone angle was used for the measurements and the experiments were carried on a standard stress-controlled rheometer (MCR 300 made by Anton Pear) at room temperature or about 22° C.

C) Freeze—Thaw Method

A quick screening rheological measurement was developed to determine the effectiveness of the freeze-thaw additives on the viscosity. Samples were loaded and the temperature sweep experiments at a constant frequency of 10 Hz and at a constant strain of 1% were performed on a MCR 300, a stress-controlled rheometer made by Anton Paar, using 50 mm diameter serrated cone with 2° cone angle at a fixed gap of 0.213 mm. Three temperature cycles were performed on each sample: (i) the cooling cycle from RT (room temperature) to 4° C. (ii) heating cycle from 4° C. to 50° C. and (iii) cooling cycle again from 50° C. to RT. Data was collected at 2° C. intervals and at each temperature, the sample was allowed to equilibrate for 1 min. The change in viscosity was determined from the initial RT viscosity to the viscosity of the sample at RT after going through the first cooling cycle.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. An aqueous, lamellar structured, skin cleaning composition comprising:
   a) about 15 to 40% by wt. of synthetic anion surfactant(s);
   b) about 5 to 30% by wt. of co-surfactant(s) selected from the group of amphoteric or nonionic surfactants or blends thereof;
   c) about 5 to 15% by wt. of $C_{12}$ to $C_{18}$ linear alkyl fatty acid(s);
   d) wherein the synthetic anionic surfactant(s): co-surfactant(s) ratio is about 0.5 to 3;
   e) wherein the synthetic anionic surfactant(s) and co- surfactant(s) to $C_{12}$ to $C_{18}$ linear alkyl fatty acid(s) ratio is about 2 to 6; and
   f) an effective amount of freeze-thaw stabilizer(s) selected from isooctanol, isotridecanol, isodecanol, polyoxyethylene(2)isooctylphenyl ether and blends thereof for maintaining at least 55% of the viscosity of the composition after one freeze-thaw cycle using the standard freeze-thaw test.

2. The composition of claim 1 wherein the viscosity either decreases continuously or increases by no more than 3 Pa.s as the composition is diluted with water at 40 C. during skin cleansing and rinsing by a consumer.

3. The composition of claim 1 wherein the pH is in the range of about 5 to 8.

4. The composition of claim 1 wherein the freeze-thaw stabilizer(s) are present in a total concentration of about 0.5 to 5% by wt.

5. The composition of claim 1 wherein the freeze-thaw stabilizer(s) have an HLB value of less than about 5.

6. The composition of claim 1 wherein the freeze-thaw stabilizer(s) have an effective molecular length of greater than about 5 but no greater than about 30 Angstroms.

7. The composition of claim 1 wherein the freeze-thaw stabilizer(s) have a melting point less than about 0° C.

8. The composition of claim 1 further comprising about 0.5 to 3% by wt. of 12-Hydroxy stearic acid.

9. The composition of claim 1 further comprising non-occlusive emollients in the concentration range of about 0.5 to 25% by wt.

10. The composition of claim 9 wherein the non-occlusive emollients are selected from glycerin, 1, 3 butanediol, or blends thereof.

11. The composition of claim 1 further comprising occlusive emollients in the concentration range of about 0.5 to 25% by wt.

12. The composition of claim 11 wherein the occlusive emollients are selected from mineral oils, tri and diglyceride oils, silicone oils, Petrolatum, paraffin wax or blends thereof.

13. The composition of claim 1 wherein the synthetic anionic surfactants are selected from Sodium lauryl ether sulfate—1EO, 2EO or 3EO, C12 acyl glycinate, Directly Esterified Fatty Isethionate (DEFI) or sodium trideceth sulfate or blends thereof.

14. The composition of claim 1 wherein the co-surfactant(s) are selected from cocamidopropyl betaine, sodium lauroyl amphoacetate, cocamidopropyl hydroxyl sultaine, alkylpoly glucoside or blends thereof.

* * * * *